United States Patent [19]

Colvin, Jr. et al.

[11] Patent Number: 4,868,767

[45] Date of Patent: Sep. 19, 1989

[54] REFLECTANCE GRADIENT DENSITOMETER

[75] Inventors: Arthur E. Colvin, Jr., Mount Airy; Stephen C. Scott, Frederick, both of Md.

[73] Assignee: Cerex Corporation, Gaithersburg, Md.

[21] Appl. No.: 79,641

[22] Filed: Jul. 30, 1987

[51] Int. Cl.$^4$ ............ G01N 33/54; G01N 21/82; G01N 33/52; G01J 3/28

[52] U.S. Cl. ............................. 364/525; 436/501; 436/165; 435/7

[58] Field of Search ........... 436/165, 170, 805, 807, 436/809, 527, 531, 529, 530; 435/58, 60, 7; 364/554, 497, 498

[56] References Cited

U.S. PATENT DOCUMENTS

| | | | |
|---|---|---|---|
| 3,709,612 | 1/1973 | Clemens | 356/178 |
| 4,240,751 | 12/1980 | Linnecke et al. | 356/409 |
| 4,405,711 | 9/1983 | Masuda et al. | 436/807 X |
| 4,482,521 | 11/1984 | Bunce et al. | 436/809 X |
| 4,556,641 | 12/1985 | Kano et al. | 436/805 X |
| 4,558,012 | 12/1985 | Nygren et al. | 436/501 |
| 4,617,277 | 10/1986 | Bohl | 436/34 |
| 4,627,014 | 12/1986 | Lo et al. | 364/497 X |
| 4,673,657 | 6/1987 | Christian | 436/807 X |
| 4,708,931 | 11/1987 | Christian | 436/807 X |
| 4,708,932 | 11/1987 | Axen et al. | 436/807 X |
| 4,761,378 | 8/1988 | Godsey | 436/809 X |

OTHER PUBLICATIONS

American Hospital Supply Corporation, Stratus ® Immunoassay System, pp. 1–12, 1986.
Kagaku Co., Ltd., Glucoscot ® II, Blood Glucose Monitor, 4 pages.
Eastman Kodak Company, Ektachem ®, 1984, 39 pages.
Behring Diagnostics, Rapimat ® Urinalysis Analyzer, 18 pages, 1984.

Primary Examiner—William L. Sikes
Assistant Examiner—Akm E. Ullah
Attorney, Agent, or Firm—Michael W. York

[57] ABSTRACT

Apparatus and method are disclosed for detecting the presence of a analyte in a sample. The apparatus includes an optical transmitter and receiver for transmitting light toward the sample and receiving a portion of the reflected light. The optical receiver acts in conjunction with a data processor to convert the reflected light to data representing the density of analyte in the sample. The apparatus thus disclosed is portable and can be transported to remote testing sites.

5 Claims, 3 Drawing Sheets

REFLECTANCE GRADIENT DENSITOMETER

BACKGROUND OF THE INVENTION

The present invention is directed, in general, toward test apparatus and, more particularly, toward apparatus for determining the presence of a analyte in a sample.

Recently, various methods have been developed for detecting a variety of analytes in a sample where the analyte is capable of reacting with a reagent to produce a particular color or hue. The color which is produced can, in turn, be detected as, for example, by using a spectrophotometric instrument.

Prior methods relied upon the detection of a analyte in a liquid cuvette, such as the well of a translucent microtiter plate. Typically, the microtiter plate included a plurality of wells each containing the liquid reactants with a minimum depth of about 70 mm through which the light must pass in order to determine the presence of analyte. Instruments used with these prior microtiter plates typically transmitted a calibrated light beam from one side of the plate through each well of the plate and detected, on the other side of the plate, the amount of light transmitted through the liquid material and the translucent plate to determine the presence of analytes contained in the liquid material.

There are currently numerous manufacturers of these plates and the associated instruments, to read the reaction occurring in the wells thereof. Plates are sold having both unmodified and modified surfaces. Some microtiter plates are pre-sensitized for use as preformulated diagnostic tools for a broad array of analytes.

When first introduced, the microtiter plate and reader systems were useful in their original design and became an industry workhorse. However, with the development of more sophisticated techniques and improved sensitivity current designs have failed to keep pace.

Some of the techniques which have become increasingly useful in detecting a analyte in a sample use antibodies. In these techniques the antibody is used to detect the presence of the analyte, in this case an antigen, for which the antibody is specific. Over the last several years, the sensitivity of antibody-based tests have increased such that less liquid volume within the wells of the microtiter plate is required. However, a need exists for a highly sensitive and inexpensive instrument to measure a reaction in a substantially liquid-free format.

SUMMARY OF THE INVENTION

It is, therefore, an object of the present invention to provide improved method and apparatus for determining the presence of a analyte in a sample.

It is a further object of the invention to provide apparatus for use in tests to determine the presence of a analyte in a sample wherein the sample and reagent can be combined and examined in the non-aqeuous state, that is, substantially free of liquid.

It is another object of the present invention to provide portable apparatus for determining the presence of an analyte in a sample.

To obtain the foregoing objects of the present invention, apparatus for detecting an analyte in a sample by reading the sample is provided. The detecting apparatus includes an emitter/detector for transmitting light along a major axis thereof and detecting the intensity of light reflected back to the emitter/detector along the axis of transmission. The emitter/detector is further adapted to provide an electrical signal which is indicative of the intensity of light received by the emitter/detector. A substantially flat laminated plate is provided for receiving the sample to be read. The laminated plate is also substantially opaque with respect to the wavelength of light transmitted by the emitter portion of the emitter/detector. A data processor is coupled to the emitter/detector for receiving the electrical signal provided by the detection portion of the emitter/detector. The data processor is adapted to process the electrical signal to determine the intensity of light reflected from the sample and perform subsequent data processing such as calculations, corrections, and unit conversions, and thereby detect the presence of analyte in a sample.

Further, a novel laminated plate for use in detecting an analyte in a sample is provided. The laminated plate of the subject invention includes a first layer of substantially flat sheet material. A second layer of material is disposed upon the first layer, the second layer providing a surface on which the detection of analyte occurs. This second layer is opaque with respect to the light transmitted from the emitter portion of the emitter/detector and detected by the detector portion of the emitter/detector. A third layer of substantially flat sheet material is mounted upon the second layer. The third layer includes a plurality of holes therein which, when mounted upon the second layer, define cells for receiving the sample material.

A novel method for detecting the presence of an analyte in a sample is disclosed. The method requires first providing a laminated plate as described above. A sample is deposited upon the laminated plate. If the sample contains an analyte which can react with the reagent, a change in intensity of reflected light occurs which is proportional to the concentration of analyte present in the sample. To determine whether a reaction has occurred between the analyte and the reagent, light is transmitted to the laminated plate such that at least a portion of the light reflected from the plate may be received. Thereafter, the intensity of light reflected from the plate is determined such that the presence of a analyte in the sample can be detected and quantitated if desired.

A major advantage of measuring the presence of analyte in a substantially non-aqueous detection format, as opposed to systems which measure analyte in a purely liquid system, is that in a substantially non-aqueous format, as disclosed for the invention, the effect of Beer's Law is comparatively insignificant. Beer's Law states that the intensity of an emergent ray of light is inversely proportional to the depth of liquid through which it travels such that the intensity of the emergent ray is diminished in an exponential manner. Thus, in systems which detect change in the emission or absorbence of light in a liquid sample, the light must pass through the liquid before reaching the detector. These systems are inherently less sensitive than a system, such as that utilized in the apparatus of the invention, where the light from the emitter does not have to pass through a liquid prior to reaching the detector.

BRIEF DESCRIPTION OF THE DRAWINGS

Subject matter which is regarded to be the invention is particularly pointed out and distinctly claimed in the numbered paragraphs appended hereto. The invention, however, both as to organization and method of practice, may best be understood from a reading of the following detailed description taken in conjunction with the drawings in which:

DETAILED DESCRIPTION OF THE PREFERRED EMBODIMENT

As mentioned above, the present invention is directed toward apparatus and method for detecting the presence of an analyte in a sample. Generally, a novel laminated plate is provided for performing the subject analyte detection tests. A sample is deposited upon the plate. Light is transmitted to the sample such that the intensity of light reflected from the sample may be determined. Data processing apparatus is provided for detecting the presence of an analyte in response to the intensity of light reflected from the sample.

The term "analyte" as used herein denotes the substance which is being detected in the sample and can be either inorganic or organic in its composition.

Figure 1A:
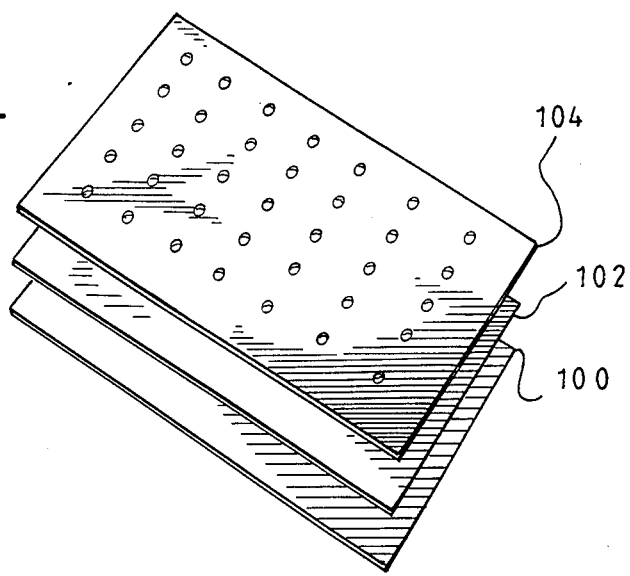
FIG. 1A is an illustrative drawing of a laminated plate constructed in accordance with the subject.

FIG. 1A shows the laminated plate which is a subject of the present invention. As shown therein, the laminated plate includes a first layer 100 of substantially flat sheet material. Preferably, sheet material 100 is substantially opaque to at least one frequency band of light as will be discussed more fully below. In the presently preferred embodiment, sheet material 100 comprises a plastic material. However, it will be apparent to those skilled in the art that various materials may be substituted for sheet material 100 without departing from the true scope of the present invention.

The laminated plate of FIG. 1A further includes a second layer 102. Layer 102 comprises a material which provides a detection surface for the analyte and which may be deposited upon layer 100 by any suitable means known in the art.

The detection surface of layer 102 can be used in an unmodified or a modified form in order to bind the analyte directly, for example, by interaction between the analyte and the material comprising layer 102, or indirectly, for example, by interaction between a coordination reagent disposed on the surface of layer 102 and the analyte.

As used herein, the term "coordination reagent" means the reagent which interacts with the analyte between the surface of layer 102 and the analyte. The coordination reagent can be a substance which interacts with the analyte in such manner as to produce the detectable change in reflected light. Alternatively, in another format, the coordination reagent acts to immobilize the analyte such that the signal reagent can interact, as described below, with the analyte to produce the detectable change in reflected light.

In a preferred embodiment, layer 102, for example, comprises an unmodified material made of nitrocellulose for direct binding of a analyte such as a protein or DNA.

The term "color" as used herein is meant to denote a change in the light absorbance or intensity occurring due to the interaction of analyte with the analyte detection reagents. As such, the term, as used herein, would also include changes in the shade of a color.

In an indirect format, a coordination reagent capable of reacting with the analyte of interest is, or will be, bound to the surface of layer 102 such that the analyte interacts directly with the coordination reagent, but only indirectly with the material comprising layer 102.

For example, a preferred coordination reagent is antibody. Techniques for preparation of polyclonal and monoclonal antibodies are well known and require no citation here. The material comprising layer 102 is selected from a material to which the antibody can be bound. A preferred material is nylon which has amino moieties or into which such moieties can be introduced by chemical means, which permit antibodies to be coupled to it by, for example, the well known glutaradehyde method. Additionally, antibodies can be coupled to glass fibers through aminosilanes. Other natural or synthetic materials, well known to those of skill in the art, which can also be used allow antibody to be coupled directly or through intermediates to the antibody.

Nitrocellulose is especially performed as a material for layer 102 since it can be used directly, as described above, or indirectly to bind a coordination reagent.

A third layer 104 is provided which, like layer 100, is a substantially flat sheet material which may be comprised of plastic. Layer 104 also includes a plurality of holes therein. When deposited upon layer 102 the preferred laminated plate will have a plurality of cells each having a nitrocellulose bottom and each adapted to receive a sample to be tested.

It will be appreciated by those skilled in the art that the method of detecting the analyte on layer 102 of the laminated plate of FIG. 1A may be performed in many different ways such that color development occurs. Thus, detectable color may occur through the direct interaction of the analyte and an unmodified or modified layer 103 or indirectly through the interaction of the analyte with the coordination reagent.

Direct analyte detection can occur through the interaction of components comprising layer 102 with the analyte resulting in a change in absorbance of the cell of layer 102. The components comprising layer 102 can, if desired, be dehydrated thereon and used to detect organic or inorganic analytes. These components can, for example, be those used in classical chemistry to detect such analytes as those of clinical and environmental importance. Thus, the detection surface can serve as a microanalytic substitute for standard wet-bench chemical analysis for detection of an analyte. Such components are well-known, or are easily discerned, by those of ordinary skill in the art and will not be further described here.

Alternatively, detectable color may occur not through the direct or indirect interactions of the analyte with layer 102, but through a second interaction between the analyte and a signal reagent.

The term "signal reagent" denotes the detectably labeled reagent which interacts with the analyte which is immobilized by the coordination reagent on layer 102. In this embodiment the analyte is, in effect, "sandwiched" between layer 102 and the signal reagent. In turn, the signal reagent can be any substance capable of interacting with the analyte if the analyte is, or will, interact with layer 102. Signal reagents can be inorganic or organic in composition. Especially preferred as organic signal reagents are antibodies which are, or will become, detectably labeled.

There are many materials to which the coordination reagent can be bound and which can be used in the present invention. Well-known materials include glass, polystyrene, polypropylene, polyethylene, dextran, nylon, amylases, natural and un-modified and modified celluloses, polyacrylamides and agaroses. Those skilled in the art will know many other suitable materials for binding the coordination reagent, or will be able to ascertain such, using routine experimentation.

The signal reagent can be coupled with a detectable label such as, for example, an enzyme. This enzyme, in turn, when later exposed to its substrate will react to the substrate in such as a manner as to produce a chemical moiety which can be detected. Examples of enzymes that can be used to detectably label are malate dehydrogenase, staphylococcal nuclease, delta 5-steriod isomerase, yeast alcohol dehydrogenase alpha-glycerophosphate dehydrogenase, triose phosphate isomerase, alkaline phosphatase, asparaginase, glucose oxidase, beta-gelactosidase, ribonuclease, urease, catalase, glucose-6-phosphate dehydrogenase, gluco-amylase, and acetylcholine esterase.

Those of ordinary skill in the art will know of other suitable labels for binding to the signal reagent, or will be able to ascertain such using routine experimentation. Furthermore, the binding of these labels to the signal reagent can be done using standard techniques common to those of ordinary skill in the art.

For purposes of the invention, the analyte which is being detected may be present in biological fluids and tissues, as well as samples derived from environmental and ecological sources.

Any sample containing a detectable yet unknown amount of analyte can be used. Thus, the sample can be a liquid (such as, for example, urine, saliva, cerebrospinal fluid, blood, serum, water and the like) or a solid or semi-solid (such as, for example, tissues, feces plant material, inorganic substrates, feeds and the like). Among the analytes which can be detected are hormones, enzymes, inflammatory agents, infectious agents, toxins, as well as such environmental contaminants as pesticides, herbicides, pollutants, or other such compounds.

Hormones are substances that act to inhibit or enhance metabolic activities. Examples of hormones of interest are those associated with reproduction such as human choriogonadotropin, luteinizing hormone and follicle-stimulating hormone, as well as hormones associated with metabolism, such as thyroid-stimulating hormones and the like.

Enzymes are protein molecules which catalyze biochemical reactions. Changes in the concentration of enzymes which are associated with certain biochemical pathways can be of valuable diagnostic significance in evaluating a disease state. Examples of enzymes of significance are most protein kinases, creatinine phosphokinase, lactate dehydrogenase, C reactive protein (CRP), serum amyloid P component (SAP), alpha-2 macroglobulin, and the like.

Inflammatory agents can be released by cells of the immune system, often following contact with an antigen. Examples of inflammatory agents include histamine, prostaglandins, thromboxane, heparin, tryptase, kininogenase and beta-glucosaminidase.

Infectious agents primarily encompass disease-causing organism of viral, bacterial or parasitic origin, Examples of such agents are those causing dengue fever, bubonic plaque, yellow fever, malaria, small pox, pneumonia and encephalitis.

Toxins are poisonous substances some of which are produced by plants, animals, or microorganisms that in sufficient dose can be debilitating or lethal. Examples of such toxins are botulin, zearalenone and *Bacillus thuringiensis* toxin.

Environmental contaminants which can be detected are pesticides, for example, diflurbenzuron, paraquat, and aldicarb sulfone; herbicides, for example, 2,4-D, alachlor, glyphosate, chlorpyrifos, and atrazine; as well as such pollutants as, for example, dioxin and polychlorinated biphenyls.

Figure 1B:
FIG. 1B is an illustrative drawing of an alternative laminated plate.

While the laminated plate of FIG. 1A is shown as a plate having a plurality of cells arranged in a two dimensional rectangular array, it will be appreciated by those skilled in the art that the laminated plate may be provided in alternative shapes and, further, that the cells of the laminated plate may be arranged in a variety of patterns. As an example, the laminated plate of FIG. 1B is shown as a substantially elongate plate including three cells linearly arranged. As another example, the laminated plate of the subject invention may further comprise a circular plate with cells arranged in a rectangular array of in a plurality of concentric circles. Other shapes and arrangements for the laminated plate and the cells thereof will readily become apparent to those skilled in the art.

Further, the laminated plate can be designed to have any number of cells. Thus, the plate could have a single cell where the detection of the analyte occurs. In this single cell format, the apparatus of the invention could be pre-programmed to contain a background absorbance value for purposes of qualitative determination of an analyte. When a quantitative determination of an analyte is performed the apparatus of the invention would also advantageously be pre-programmed with an upper absorbance value in order to allow quantitation of the absorbance occuring in the cell.

Again referring to the drawing of FIG. 1b, it is noted that the laminated plate illustrated therein contains notches on each of its sides. These notches are provided to cooperate with other components of the densitometer (other components not shown) to provide a detent means for orienting the laminated plate with the densitometer to ensure proper alignment of the plate cells with the densitometer optics. Other components for cooperating with the notches of the plate shown in FIG. 1B will readily come to mind to those skilled in the art. Further, other detent means will readily be apparent to those skilled in the art. Also, means for providing orientation between the densitometer and plates of varying shapes will be apparent to those skilled in the art.

Figure 2:
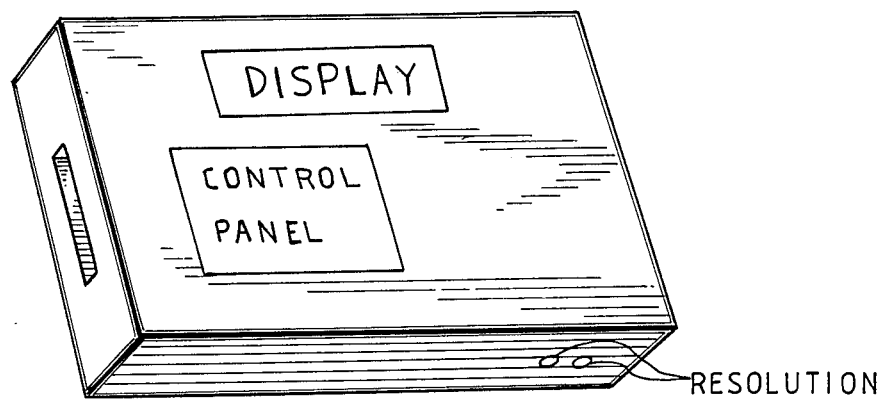
FIG. 2 is an illustration of the spectrophotometric densitometer which is the subject of the present invention.

A particular advantage provided by the subject invention is that the analyte detection tests can be performed using portable test apparatus in a field environment. FIG. 2 is an illustration of a portable densitometer built in accordance with the subject invention. The detection apparatus of FIG. 2 measures approximately 4 in. ×5 in. ×2 in. Hence, this apparatus may be easily transported to any location convenient for performing the analyte detection tests of the subject invention. As an example, the apparatus of FIG. 2 may be carried by military personnel and used for the detection of, for example, toxic and pathogenic substances, commonly used in chemical and biological warfare.

Figure 3:
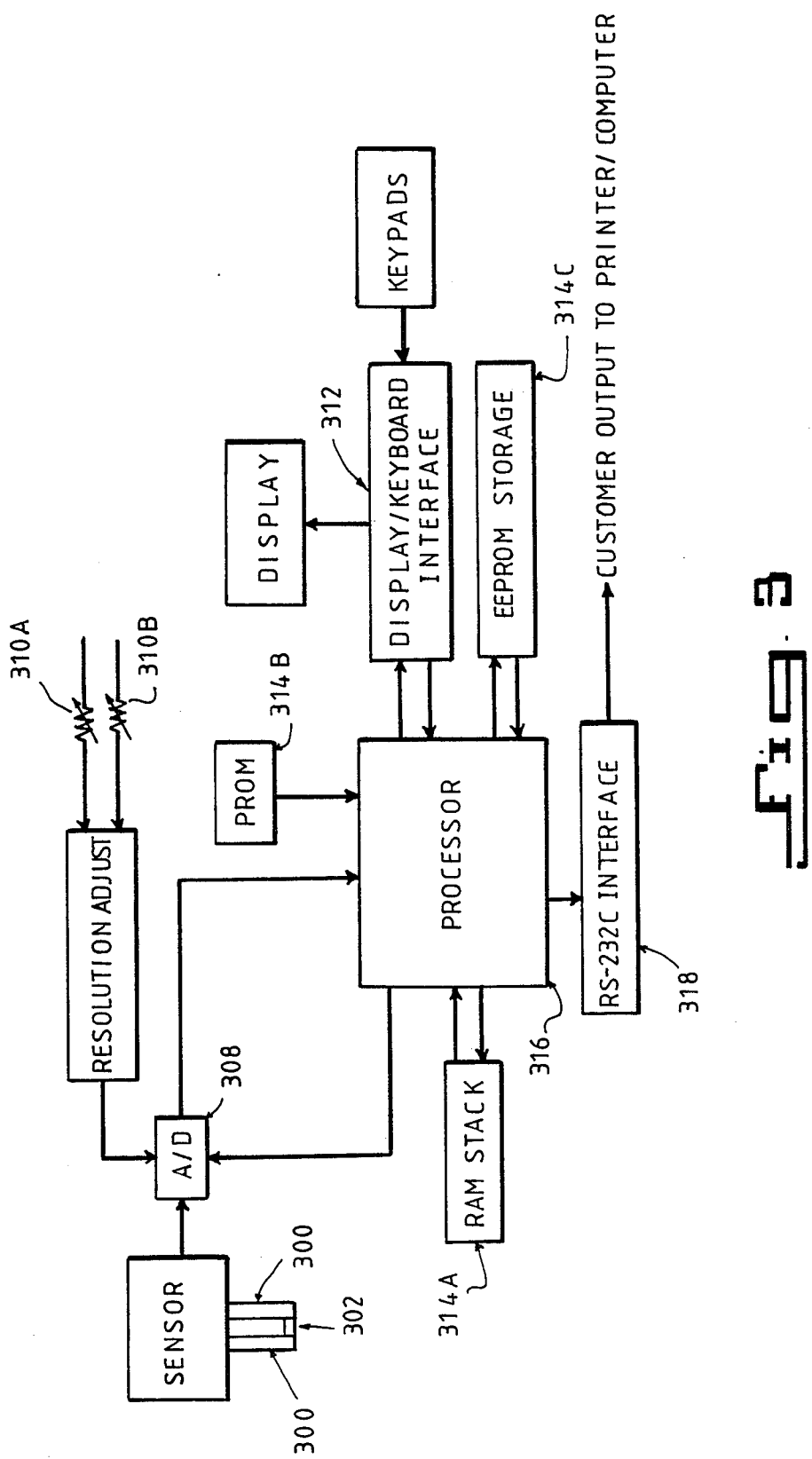
FIG. 3 is an illustrative block diagram of the densitometer which is the subject of the present invention.

With reference to FIG. 3, there is provided a more illustrative block diagram of the display control and interface apparatus of FIG. 2. Therein, the analyte detection unit is shown to comprise an optical transmitter 300 coupled to a voltage source $V_s$ for transmitting light of a predetermined bandwidth along a major axis thereof. An optical receiver 302 is provided for receiving at least a portion of the light reflected from the laminated plate. As discussed above, the laminated plate includes detent means for orienting the plate with the densitometer and thereby insure proper alignment of optical transmitter 300 and optical receiver 302 with the cells of the laminated plate.

Optical transmitter 300 and optical receiver 302 are preferrably provided in a combined unit. In the presently preferred embodiment, optical transmitter 300 and optical receiver 302 are provided in a combined concentrically arranged emitter/detector unit wherein optical receiver 302 is in the center. The use of a combined emitter/detector in which the emitter and detector portions thereof are concentrically arranged has significant advantages over systems utilizing spatially discrete and separate emitter and detector units.

For example, a problem associated with reading reflected light from a solid surface when separate emitter and detector units are used is that the topographical non-homogeneity of the reflectance surface creates problems with respect to reproducibility from one surface area to another. When a combined emitter/detector, such as that of the invention is used, these non-homogeneities are cancelled out due to the fact that the emitter portion completely encircles the reflectance surface such that the reflectance surface is exposed to the incident light from the emitter from about 360°. As a consequence, any non-homogeneities in surface topography are cancelled by using the combined emitter/detector described in the apparatus of the invention.

Optical receiver 302 is adapted to provide an electrical signal to an analog-to-digital (A/D) converter 308. The electrical signal provided from optical receiver 302 is indicative of the intensity of light received thereby and is, therefore, indicative of the intensity of light reflected from the sample contained on the laminated plate. Optical transmitter 300 and receiver 302 may comprise any means for transmitting light in a predetermined bandwidth as is known in the art.

A/D converter 308 responds to the electrical signal to provide a digital signal indicative of the magnitude of voltage received from optical receiver 302. A shown in the presently preferred embodiment, A/D converter 308 provides ten-bit binary signal in response to the electrical signal received from optical receiver 302. A/D converter 308 also includes a reference voltage input which is coupled to a variable resistor 310A as well as a scaling resistor 310B. The reference input to A/D converter 308 requires a voltage for adjusting the range of voltage expected from receiver 302. Var. resistor 310A may be adjusted by a resolution input (see FIG. 3) which is available to the user of the analyte detection apparatus. Scaling resistor 310B is set for the voltage range desired as dictated by the physical tests performed, wherein each resistor is separately coupled to A/D converter 308.

A/D converter 308 provides its output to a display and control unit 312 and memory unit 314A via a microprocessor 316. Display and control unit 312 is shown as a single device but may comprise a plurality of electrical switches and a digital display as is known in the art. Also, display and control unit 312 may comprise a digital control device for interfacing the display and control unit with the remainder of the analyte detection circuit.

Memory 314 comprises means for storing the data received from A/D converter 308. Additionally, memory 314B comprises read only memory (ROM) for storing instructions which are used by a microprocessor 316. Microprocessor 316 is adapted for receiving instructions and data from memory 314B and controlling the analyte detection circuit as described herein. Microprocessor 316 is coupled to an interface 318 which is provided for interfacing the analyte detection circuit shown in FIG. 3A with an external data processing system. Interface 318 may comprise a commercially available connection unit such as an RS-232.

In operation, a sample is placed on the laminated plate which is placed in the spectrophotometric densitometer which is the subject of the present invention. In one preferred embodiment discussed above, the laminated plate includes detent means for aligning the cell of the laminated plate with the optics of the densitometer. The densitometer may be adapted to initiate the test in response to proper insertion of the laminated plate or, alternatively, may be adapted to start the test in response to a user provided input. Each of the foregoing methods for initiating the test may be readily implemented by those skilled in the art. Further, other methods and apparatus for initiating the test will be apparent to those skilled in the art.

Upon initiation of the test, optical transmitter 300 transmits light in a predetermined bandwith toward the sample contained in the cell which has been aligned for testing. At least a portion of the light transmitted toward the sample is reflected back toward optical receiver 302. In response to the received light, optical receiver 302 provides an electrical signal to A/D converter 308. The magnitude of the electrical signal is proportional to the intensity of light received. A/D converter 308 converts this electrical signal to a digital signal wherein the value of the digital signal is indicative of the magnitude of the electrical signal provided by receiver 302.

Microprocessor 316 controls memory 314C to store the information received from A/D converter 308. The densitometer is first calibrated by storing a lower bound value corresponding to zero percent concentration and storing an upper bound value corresponding to one hundred percent concentration. The calibration samples may be predeposited upon a calibration laminated plate provided to calibrate the densitometer. Alternatively, each plate may contain its own calibration samples. As an example, the plate of FIG. 1B, which contains three cells, may have the calibration samples deposited in the first two cells leaving the third cell vacant for the test sample. In any event, microprocessor 316 will store the calibration values in predetermined storage locations within memory 314C.

Further, as mentioned above, the densitometer may be adjusted to alter its measurement resolution. While this calibration may be performed at a test site remote from the user's laboratory, it is suggested that the resolution be set once before any tests begin. This is preferrably done at the user's laboratory.

After each test value is received for A/D converter 308, microprocessor 316 determines the corresponding percentage of the calibration range and stores the value along with the determined percentage in a memory location associated with that test. In the preferred embodiment, each test is recorded in the order taken, i.e., the first values stored in memory are stored in a location associated with first test and so on. As the data is retrieved from memory the number of the test is also provided by the densitometer.

A particular advantage of the present invention is that EEPROM memory (314C) is utilized such that the unit may be used for field tests. After microprocessor 316 stores each value, power need not be continuously provided to the memory to maintain the data. As such, the densitometer may be transported from test site to test site with no apparent power drainage.

After all tests are taken and the data recorded in memory, the densitometer is adapted to communicate with other external data processors or other output devices used to print or tally via interface 318. The user need only couple the external data processor to the interface and provide the appropriate instructions to the densitometer.

While only several presently preferred embodiments have been described in detail herein, it will be apparent to those skilled in the art that many modifications and variations are possible without departing from the true scope and spirit of the invention. It is the intent of the applicants to protect all such variations and modifications by the claims appended hereto.

We claim:

1. Apparatus for detecting the presence of an analyte in a sample by reading the sample, said apparatus comprising:

emitter/detector means for transmitting light along a major axis thereof and detecting the intensity of light reflected back to said emitter/detector means along said axis, said emitter/detector means being adapted to provide an electrical signal indicative of the intensity of light received by said emitter/ detector means;

laminated plate means having a substantially flat surface for receiving the sample to be read, said laminated plate means being adapted to reflect the frequency of light transmitted by said emitter/detector means; and data processing means coupled to said emitter/detector means for receiving the electrical signal provided by said emitter/detector means and for processing said electrical signal to determine the intensity of light reflected from the sample to be read and thereby detect the presence of an analyte in the sample, said data processing means comprising analog/digital (A/D) conversion means for converting the electrical signal received from said emitter/ detector means to a digital signal including means for adjusting the range of voltage to be received from said emitter/detector means located to be readily accessible by a user such that the user may adjust the resolution of said data processing means and program means for executing a program to control said data processing means including range means such that the user may adjust the range of digital signals which said data processing means considers from about 0 to 99%.

2. Apparatus as recited in claim 1 further comprising:

housing means for mounting said emitter/detector means, said housing being adapted to receive said plate means; and means for aligning said plate means with said emitter/detector means such that light transmitted by said emitter detector means is at least partially reflected by the material to be read.

3. Apparatus as recited in claim 2 wherein said aligning means includes detector means for holding said plate means in a predetermined relations with said housing means.

4. Apparatus as recited in claim 2 wherein said housing means is further adapted to house said data processing means.

5. Apparatus as recited in claim 4 wherein said range of voltage adjusting means is mounted in said housing means.

* * * * *